(12) United States Patent
Fujioka et al.

(10) Patent No.: US 11,549,130 B2
(45) Date of Patent: Jan. 10, 2023

(54) RANDOM INTERESTERIFICATION LIPASE

(71) Applicant: AMANO ENZYME INC., Nagoya (JP)

(72) Inventors: Hiroki Fujioka, Kakamigahara (JP); Saki Norifune, Kakamigahara (JP); Tatsuya Hamada, Kakamigahara (JP); Tetsuya Takahashi, Kakamigahara (JP); Yusuke Tanaka, Kakamigahara (JP); Toru Katase, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

(21) Appl. No.: 16/968,261

(22) PCT Filed: Dec. 27, 2018

(86) PCT No.: PCT/JP2018/048378
§ 371 (c)(1),
(2) Date: Aug. 7, 2020

(87) PCT Pub. No.: WO2019/155790
PCT Pub. Date: Aug. 15, 2019

(65) Prior Publication Data
US 2020/0370077 A1    Nov. 26, 2020

(30) Foreign Application Priority Data
Feb. 9, 2018   (JP) .............................. JP2018-022487

(51) Int. Cl.
*C12P 7/64*   (2022.01)
*C12N 9/20*   (2006.01)

(52) U.S. Cl.
CPC ................ *C12P 7/64* (2013.01); *C12N 9/20* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 2007/0231446 A1 | 10/2007 | Nagasawa et al. | |
| 2010/0048909 A1* | 2/2010 | Mori | C07C 231/18 548/239 |

FOREIGN PATENT DOCUMENTS

| | | |
|---|---|---|
| JP | H01-501120 A | 4/1989 |
| JP | H02-092281 A | 4/1990 |
| JP | H08-066186 A | 3/1996 |
| JP | 2005-185290 A | 7/2005 |
| JP | 3791943 B2 | 6/2006 |
| JP | 2008-194011 A | 8/2008 |
| WO | 1988/002775 A1 | 4/1988 |
| WO | 2006/059592 A1 | 6/2006 |
| WO | 2012/077614 A1 | 6/2012 |

OTHER PUBLICATIONS

Singh et al. (Curr. Protein Pept. Sci. 18:1-11, 2017 (Year: 2017).*
Zhang et al., Structure 26:1474-1485, 2018 (Year: 2018).*
Wataru Matsumoto, "Interesterification of Fats and Oils," Journal of Japan Oil Chemists' Society, 48, 1999, pp. 1151-1159 and its English abstract. (discussed in the spec).
Toru Nezu et al. "Recent Development of Fat Modification Process," Oleoscience, vol. 6, No. 3, 2006, pp. 145-151 and its English abstract. (discussed in the spec).
A. R. Macrae, "Lipase-Catalyzed Interesterification of Oils and Fats," J. Am. Oil Chem. Soc., vol. 60, No. 2, Feb. 1983, pp. 291-294. (discussed in the spec).
O.M. Lai et al., "Physical Properties of Pseudomonas and Rhizomucor miehei Lipase-Catalyzed Transesterified Blends of Palm Stearin:Palm Kernel Olein," J. Am. Oil Chem. Soc., 75, No. 8, 1998, pp. 953-959. (discussed in the spec).
F. Arous et al., "Newly isolated yeasts from Tunisian microhabitats: Lipid accumulation and fatty acid composition," Engineering in Life Sciences, 17, 2017, pp. 226-236. (cited in the ISR).
International Search Report dated Mar. 19, 2019, issued for PCT/JP2018/048378.
Supplementary European Search Report dated Oct. 29, 2021, issued for counterpart European Patent Appln. No. 18904906.7.
S. Benjamin et al., "Candida Rugosa Lipases: Molecular Biology and Versatility in Biotechnology", Yeast, vol. 14, No. 12, Sep. 15, 1998, pp. 1069-1087. (cited in the Oct. 29, 2021 Search Report issued for EP18904906.7).
P. Dominguez De Maria et al., "Understanding Candida rugosa lipases: An overview", Biotechnology Advances, vol. 24, No. 2, Mar. 1, 2006, pp. 180-196. (cited in the Oct. 29, 2021 Search Report issued for EP18904906.7).
Database UniProt [Online], "SubName: Full=Triacylglycerol lipase {ECO:0000313'EMBL:EGY77036.1}; EC=3.1.1.3{ECO:00003131EMBL:EGY77036.1};" Dec. 14, 2011, XP055853084. (cited in the Oct. 29, 2021 Search Report issued for EP18904906.7).
Database EMBL [Online], "Lawsonella clevelandensis strain X1698 chromosome, complete genome.", Oct. 9, 2015, XP55853098, retrieved from EBI accession No. EM STD:CP012390 Database accession No. CP012390 sequence (cited in the Oct. 29, 2021 Search Report issued for EP18904906.7).
Ana Carolina Barbosa Padovan et al., "Systematic review and new insights into the molecular characterization of the *Candida rugosa* species complex", Fungal Genetics and Biology, vol. 61, Oct. 22, 2013, pp. 33-41. (cited in the Oct. 29, 2021 Search Report issued for EP18904906.7).

* cited by examiner

*Primary Examiner* — David Steadman
(74) *Attorney, Agent, or Firm* — Locke Lord LLP

(57) ABSTRACT

An object of the present invention is to provide an enzyme showing random transesterification ability, which is suitable for food applications. Provided is a random transesterification lipase having high heat resistance in oils and fats.

7 Claims, 8 Drawing Sheets
Specification includes a Sequence Listing.

RANDOM INTERESTERIFICATION LIPASE

The specification incorporates by reference herein the material in the Sequence Listing recited in the 9 KB ASCII text file submitted on Aug. 7, 2020 and named "1476161.223US9 - AE17005Pamano_ST25.txt."

TECHNICAL FIELD

The present invention relates to a random transesterification lipase and use thereof. The present application claims priority based on Japanese Patent Application No. 2018-022487 filed on Feb. 9, 2018, the entire contents of which are incorporated herein by reference.

BACKGROUND ART

Transesterification reactions of oils and fats are effective methods for modifying the physical properties of oils and fats (melting point, crystallinity, heat resistance, etc.), and are roughly classified into two groups, chemical transesterification and enzymatic transesterification (see, for example, NPLs 1 and 2). The chemical transesterification has many problems such as high environmental load and poor work safety. In recent years, due to concern about the health risk of trans-fatty acids, attention has been paid to the manufacture of transesterified oils and fats as an alternative to partial hydrogenation that causes the production of trans-fatty acids, and the demand for enzymatic random transesterification reactions is increasing. It is said that, for the enzymatic random transesterification, lipases derived from the genera *Candida, Alcaligenes, Pseudomonas, Humicola* (trade name: Novozymes, Lipozyme TL IM), and the like can be used (see, for example, PTLs 1 to 3 and NPLs 3 and 4). The present applicant reported, in the previous patent application (PTL 4), a novel lipase derived from a microorganism of the genus *Geobacillus* showing random transesterification ability.

CITATION LIST

Patent Literature

[PTL 1] WO 2006/059592
[PTL 2] JP 3791943 B
[PTL 3] JP 2008-194011 A
[PTL 4] WO 2012/077614

Non Patent Literature

[NPL 1] Journal of Japan Oil Chemists' Society, 48, 1151-1159 (1999)
[NPL 2] Oleoscience, 6, 145-151 (2006)
[NPL 3] J. Am. Oil Chem. Soc., 60, 291-294 (1983)
[NPL 4] J. Am. Oil Chem. Soc., 75, 953-959 (1998)

SUMMARY OF INVENTION

Technical Problem

Especially in food applications, the need for the enzymatic random transesterification is high. However, an enzyme that can be used in food applications has not been put into practical use. An object of the present invention is to provide an enzyme (random transesterification lipase) suitable for food applications in order to overcome this situation.

Solution to Problem

The present inventors have conducted large-scale screening targeting about 1,500 strains of microorganisms (bacteria, yeast, filamentous fungi, actinomycetes, etc.) in order to find a random transesterification lipase suitable for food applications. As a result of stepwise screening with originality and ingenuity, the present inventors have succeeded in obtaining and identifying an enzyme with high random transesterification activity and excellent heat resistance in oils and fats (heat-resistant random transesterification lipase). Furthermore, the present inventors have succeeded in identifying the amino acid sequence of the enzyme and the base sequence of a gene encoding the enzyme. The following inventions are based on these achievements.

[1] A lipase having the following enzymological properties:
(1) action: catalyzing a random transesterification reaction;
(2) molecular weight: having a molecular weight without N-glycan of about 36 kDa (by SDS-PAGE);
(3) temperature stability in oils and fats: being stable at 60° C. or lower (by evaluation using tricaprylin and methyl stearate as substrates and also using the amount of methyl caprylate produced as an index); and
(4) reactivity in oils and fats: showing the highest reactivity at 80° C. when allowed to react at 40 to 80° C. (by evaluation using cacao butter as a substrate and also using the amount of tripalmitin produced as an index).

[2] The lipase according to [1], further having the following enzymological properties:
(5) pH stability: being stable in the pH range of 3 to 7 (30° C. and 1 hour); and
(6) optimum pH: 6.

[3] The lipase according to [1] or [2], wherein the N-terminal amino acid sequence is VTDEPLENVPGILSHPTI (SEQ ID NO: 1).

[4] The lipase according to any one of [1] to [3], which is derived from *Candida pararugosa*.

[5] The lipase according to [4], wherein *Candida pararugosa* is an NBRC 0966 strain or a mutant strain thereof.

[6] A lipase having an amino acid sequence shown in SEQ ID NO: 2 or an amino acid sequence equivalent to the amino acid sequence.

[7] The lipase according to [6], wherein the equivalent amino acid sequence is an amino acid sequence having 70% or more identity with the amino acid sequence shown in SEQ ID NO: 2.

[8] An enzyme preparation comprising the lipase according to any one of [1] to [7].

[9] A random transesterification method for oils and fats, including a step of allowing the lipase according to any one of [1] to [7] to act on oils and fats.

[10] A method for manufacturing a lipase for random transesterification, including the following steps (1) and (2):
(1) culturing *Candida pararugosa*; and
(2) collecting a lipase from a culture solution and/or cell bodies after the culture.

[11] The manufacture method according to [10], wherein *Candida pararugosa* is an NBRC 0966 strain.

[12] A method for manufacturing a random transesterified oil or fat, including a step of allowing the lipase according to any one of [1] to [7] to act on an oil or fat.

[13] A lipase gene comprising any DNA selected from the group consisting of the following (a) to (c):

(a) a DNA encoding an amino acid sequence of SEQ ID NO: 2 or an amino acid sequence equivalent to the amino acid sequence;

(b) a DNA consisting of a base sequence of SEQ ID NO: 4 or 5; and (c) a DNA having a base sequence equivalent to the base sequence of SEQ ID NO: 4 or 5 and also encoding a protein having random transesterification activity.

[14] A recombinant DNA comprising the lipase gene according to [13].

[15] A microorganism possessing the recombinant DNA according to [14].

[16] A method for manufacturing a lipase, including the following steps (i) and (ii):

(i) culturing the microorganism according to [15] under conditions where a protein encoded by the gene is produced; and (ii) collecting the produced protein.

DESCRIPTION OF EMBODIMENTS

1. Terminology

Figure 1:
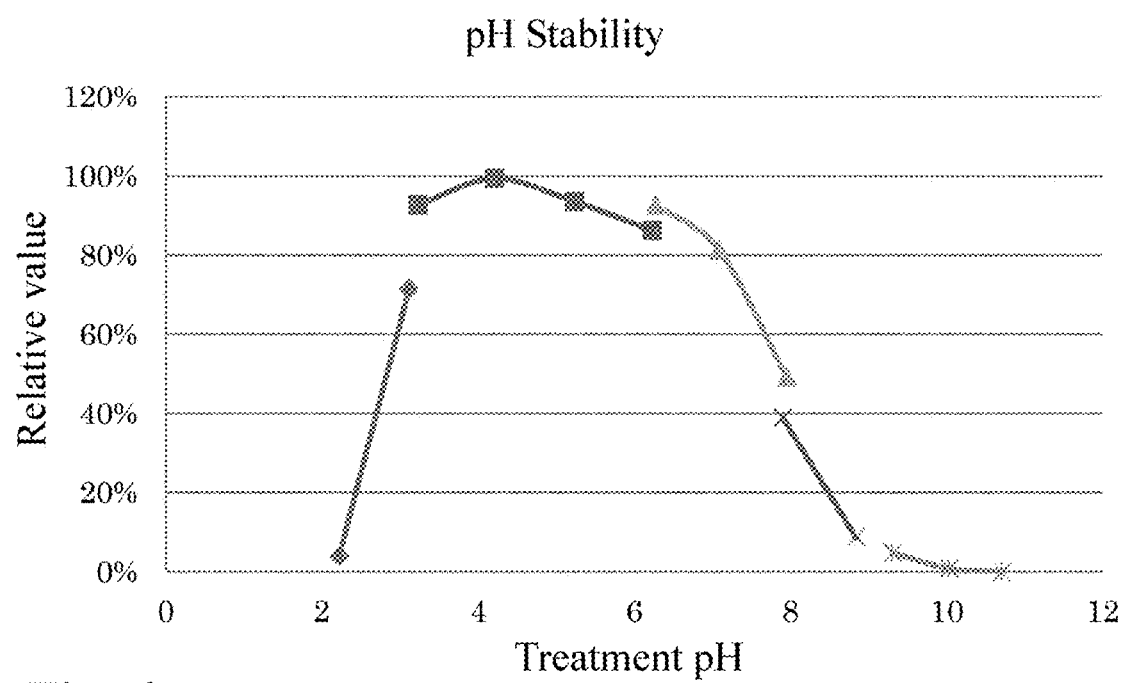
FIG. 1 pH Stability of a novel lipase derived from a *Candida pararugosa* NBRC 0966 strain.

The term "isolated" as used herein is used exchangeably with "purified." The term "isolated" is used to distinguish a material in a natural state, i.e., in a state in which it occurs in nature, from the material in a state in which it does not occur in nature. By a man-made operation of isolating a material of interest, the material will be in an "isolated state," which is a state different from its natural state. A material that has been isolated is clearly and determinately different from the material itself found in nature.

The purity of an isolated enzyme is not particularly limited. However, if an isolated enzyme is intended to be used for applications requiring that the enzyme be of high purity, then it is preferable that the isolated enzyme have a higher purity.

2. Novel Lipase

A first aspect of the present invention relates to a novel lipase successfully obtained and identified and found to be useful by the present inventors. The lipase of the present invention (hereinafter, referred to also as "the present enzyme") is characterized by having the following enzymological properties.

(1) Action

The present enzyme is a lipase and catalyzes a random transesterification reaction. The random transesterification activity can be evaluated by a method using cacao butter (cacao oil) as a substrate ("Random transesterification activity measurement method" which will be described later). Cacao butter contains oleic acid, palmitic acid, stearic acid, and the like as constituent fatty acids, and contains, as the main ingredient, a triglyceride having oleic acid bound mainly at the 2-position. Therefore, tripalmitin (PPP) in which palmitic acid is bound to all of the 1-, 2-, and 3-positions is produced only by a random transesterification reaction (palmitic acid at the 1- or 3-position must be exchanged with oleic acid at the 2-position, and, when the reaction is caused with a lipase specific for the 1- and 3-positions, no triglyceride with palmitic acid inserted into the 2-position is produced). Therefore, the random transesterification activity can be evaluated using the amount of tripalmitin produced as an index. It can be said that a random transesterification reaction is catalyzed if the production ratio of tripalmitin (C48) is increased by the reaction when the activity is evaluated by a random transesterification activity measurement method which will be described below. The degree of increase is not particularly limited, but it is desired that ΔPPP (%) is preferably 0.01 or more, more preferably 0.03 or more, further preferably 0.05 or more.

(2) Molecular Weight

The present enzyme contains sugar chains (that is, a glycoprotein) in its native form (when produced by *Candida pararugosa*), and the molecular weight of the present enzyme after removal of N-glycans, that is, when the present enzyme does not contain any N-glycan, is about 36 kDa (molecular weight measured by SDS-PAGE).

(3) Temperature Stability in Oil and Fat

The temperature stability in oils and fats can be evaluated by a method using tricaprylin and methyl stearate as substrates and also using the amount of methyl caprylate produced as an index (details thereof will be described later). When treated in tricaprylin for 1 hour, the enzyme of the present invention maintains an activity of 90% or higher at 60° C. or lower. The present enzyme showing such excellent temperature stability is suitable for food applications which require treatment at relatively high temperatures (for example, processing of oils and fats having a high melting point).

(4) Reactivity in Oil and Fat

The reactivity in oils and fats can be evaluated by a method using cacao butter as a substrate and also using the amount of tripalmitin produced as an index (details thereof will be described later). When allowed to react in oils and fats at 40 to 80° C., the present enzyme shows the highest reactivity at 80° C. Such high reactivity at high temperatures is suitable for food applications that require treatment at relatively high temperatures (for example, processing of oils and fats having a high melting point).

The present enzyme can be further characterized by the following enzymological properties (5) and (6).

(5) pH Stability

The present enzyme shows stable activity at a pH of 3 to 7. For example, if the pH of the enzyme solution to be treated is within the range of 3 to 7, the present enzyme shows 80% or more of the maximum activity after treatment at 30° C. for 1 hour. The pH stability is determined based on the results of measurement, for example, in a glycine-hydrochloric acid buffer solution in the pH range of 2 to 3, in a citrate buffer solution in the pH range of 3 to 6, in a phosphate buffer solution in the pH range of 6 to 8, in a Tris-hydrochloric acid buffer solution in the pH range of 8 to 9, and in a sodium carbonate buffer solution in the pH range of 9 to 11.

(6) Optimum pH

The optimum pH of the present enzyme is 6. The optimum pH is determined, for example, based on the results of measurement in a Britton-Robinson's buffer solution (pH 2 to 9).

The present enzyme can be further characterized by its origin, i.e., "*Candida pararugosa*". The phrase "derived from *Candida pararugosa*" means a lipase produced by a microorganism classified as *Candida pararugosa* (which may be a wild strain or a mutant strain) or a lipase obtained by a genetic engineering method using the lipase gene of *Candida pararugosa* (which may be a wild strain or a mutant strain). Therefore, a recombinant produced by a host microorganism into which the lipase gene acquired from *Candida pararugosa* (or a gene obtained by modifying the gene) or a gene having a base sequence equivalent to that of the lipase gene is introduced also corresponds to the lipase derived from *Candida pararugosa*. For convenience of explanation, *Candida pararugosa* from which the present enzyme is derived is referred to as microorganism from which the present enzyme is derived. In addition, the microorganisms used to produce the present enzyme (*Candida pararugosa* and host microorganism) are referred to as producer strain.

A specific example of *Candida pararugosa* is an NBRC 0966 strain. The NBRC 0966 strain is a strain (published as NBRC 0966 in the NBRC Culture catalog) stored in the National Institute of Technology and Evaluation (2-5-8 Kazusakamatari, Kisarazu, Chiba), and can be obtained through prescribed procedures.

The analysis of the amino acid sequence of a purified enzyme (lipase) derived from the NBRC 0966 strain has revealed that the N-terminal amino acid sequence is VTDEPLENVPGILSHPTI (SEQ ID NO: 1). Based on this fact, the present enzyme can be further characterized by the N-terminal amino acid sequence. The present enzyme is characterized in that it contains an amino acid sequence of SEQ ID NO: 1 or an amino acid sequence equivalent to the amino acid sequence at the N-terminal.

As a result of further studies by the present inventors, the amino acid sequence of the lipase produced by the NBRC 0966 strain (SEQ ID NO: 2) has been determined. Therefore, one embodiment of the present invention is characterized in that the lipase is composed of a protein having an amino acid sequence shown in SEQ ID NO: 2. Here, in general, when a part of the amino acid sequence of a certain protein is modified, the modified protein may have the same function as the unmodified protein. The modification of the amino acid sequence may not substantially affect the function of the protein, and the function of the protein may be maintained before and after the modification. Therefore, as another embodiment, the present invention provides a protein having an amino acid sequence equivalent to the amino acid sequence shown in SEQ ID NO: 2 and also having random transesterification activity (hereinafter, also referred to as "equivalent protein").

The "equivalent amino acid sequence" in the present specification refers to an amino acid sequence which is partially different from the reference sequence (amino acid sequence of SEQ ID NO: 1 or amino acid sequence of SEQ ID NO: 2), but in which the difference does not substantially affect the function (herein, random transesterification ability) of the protein. Therefore, when the amino acid sequence of SEQ ID NO: 1 is used as a reference, an enzyme having an equivalent amino acid sequence as the N-terminal amino acid sequence catalyzes a random transesterification reaction. The degree of activity is not particularly limited as long as the function as a random transesterification lipase can be exerted. However, it is preferable that the activity be equivalent to or higher than that of the enzyme having the reference sequence at the N-terminal. Similarly, when the amino acid sequence of SEQ ID NO: 2 is used as a reference, an enzyme having an equivalent amino acid sequence catalyzes a random transesterification reaction. The degree of activity is not particularly limited as long as the function as a random transesterification lipase can be exerted. However, it is preferable that the activity be equivalent to or higher than that of the enzyme having the reference amino acid sequence (SEQ ID NO: 2).

When the amino acid sequence of SEQ ID NO: 1 is used as a reference, the "partial difference in amino acid sequence" means that, typically, a mutation (change) in amino acid sequence occurs due to deletion or substitution of one to several (upper limit is, for example, 2, 3, or 4) amino acids constituting the amino acid sequence, addition or insertion of one to several (upper limit is, for example, 2, 3, or 4) amino acids, or a combination thereof. The difference in amino acid sequence herein is allowed as long as the random transesterification ability is retained (the activity may slightly vary). As long as this condition is satisfied, the position of the difference in amino acid sequence is not particularly limited, and the difference in amino acid sequence may occur at a plurality of positions. That is, when the amino acid sequence of SEQ ID NO: 1 is used as a reference, the equivalent amino acid sequence has, for example, about 75% or more, preferably about 80% or more, more preferably about 85% or more, even more preferably about 90% or more, most preferably about 95% or more identity. The difference in amino acid sequence may occur at a plurality of positions.

When the amino acid sequence of SEQ ID NO: 2 is used as a reference, the "partial difference in amino acid sequence" means that, typically, a mutation (change) in amino acid sequence occurs due to deletion or substitution of one to several (upper limit is, for example, 2, 3, 4, 5, 6, 7, 8, or 9) amino acids constituting the amino acid sequence, addition or insertion of one to several (upper limit is, for example, 2, 3, 4, 5, 6, 7, 8, or 9) amino acids, or a combination thereof. The difference in amino acid sequence herein is allowed as long as the random transesterification ability is retained (the activity may slightly vary). As long as this condition is satisfied, the position of the difference in amino acid sequence is not particularly limited, and the difference in amino acid sequence may occur at a plurality of positions. The "plurality" herein is, for example, a number corresponding to less than about 30% of all the amino acids, a number corresponding to less than about 20% thereof, a number corresponding to less than about 15% thereof, or a number corresponding to less than about 10% thereof, and is preferably a number corresponding to less than about 5% thereof, more preferably a number corresponding to less than about 3% thereof, even more preferably a number corresponding to less than about 2% thereof, most preferably a number corresponding to less than about 1% thereof. That is, the equivalent protein has, for example, about 70% or more, about 80% or more, about 85% or more or about 90% or more, preferably about 95% or more, more preferably about 97% or more, even more preferably about 98% or more, most preferably about 99% or more identity with the reference amino acid sequence (higher percentages of identity are preferred). The difference in amino acid sequence may occur at a plurality of positions.

Preferably, conservative amino acid substitution occurs at the amino acid residues that are not essential for random transesterification ability to obtain an equivalent amino acid sequence. The term "conservative amino acid substitution" as used herein refers to substitution of an amino acid residue with an amino acid residue having a side chain with similar properties. Amino acid residues are classified into several families depending on their side chains: a basic side chain (for example, lysine, arginine, and histidine); an acidic side chain (for example, aspartic acid and glutamic acid); an uncharged polar side chain (for example, glycine, asparagine, glutamine, serine, threonine, tyrosine, and cysteine); a non-polar side chain (for example, alanine, valine, leucine, isoleucine, proline, phenylalanine, methionine, and tryptophan); a beta-branched side chain (for example, threonine, valine, and isoleucine); and an aromatic side chain (for example, tyrosine, phenylalanine, tryptophan, and histidine). The conservative amino acid substitution is preferably substitution between amino acid residues within the same family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence of the present enzyme, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package, with the gap weight of 50, and the gap length weight of 3.

The present enzyme may be a portion of a larger protein (for example, a fused protein). Examples of the sequence added to a fused protein include the sequences useful for purification of multiple histidine residues, and addition sequences which ensures stability in recombination production.

The present enzyme having the above-described amino acid sequence is readily prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA encoding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

3. Enzyme Preparation

The present enzyme is provided, for example, in the form of an enzyme preparation. The enzyme preparation may contain an excipient, a buffer agent, a suspending agent, a stabilizer, a preservative, an antiseptic, saline and the like besides the active ingredient (i.e. the present enzyme). The degree of purity of the present enzyme is not particularly limited. Thus, the present enzyme may be a crude or purified enzyme. As the excipient, lactose, sorbitol, D-mannitol, maltodextrin, white soft sugar and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

4. Nucleic Acid and the Like Encoding the Present Enzyme

A second aspect of the present invention provides a nucleic acid related to the present enzyme. Specifically, there are provided a gene encoding the present enzyme, a nucleic acid that can be used as a probe for identifying the nucleic acid encoding the present enzyme, and a nucleic acid that can be used as a primer for amplifying or mutating the nucleic acid encoding the present enzyme.

The gene encoding the present enzyme is typically used in preparation of the present enzyme. According to a genetic engineering procedure using the gene encoding the present enzyme, the present enzyme in a more homogeneous state can be obtained. Further, the method can be a preferable method also in the case of preparing a large amount of the present enzyme. Note that uses of the gene encoding the present enzyme are not limited to preparation of the present enzyme. For example, the nucleic acid can also be used as a tool for an experiment intended for clarification of action mechanisms of the present enzyme or a tool for designing or preparing a mutant of the present enzyme.

The "gene encoding the present enzyme" in the present specification refers to a nucleic acid that provides the present enzyme when expressed, including not only a nucleic acid having a base sequence corresponding to the amino acid sequence of the present enzyme, but also a nucleic acid in which a sequence that does not encode the amino acid sequence is added to such a nucleic acid. Also, degeneracy of codons is taken into consideration. For a nucleic acid having a base sequence containing no start codon, the present enzyme can be obtained by adding a start codon or a signal peptide containing a start codon before expression.

Examples of the sequence of the gene encoding the present enzyme are shown in SEQ ID NO: 4 (a cDNA sequence encoding the sequence of a mature (amino acid sequence of SEQ ID NO: 2), which does not include a signal sequence) and SEQ ID NO: 5 (a cDNA sequence encoding a sequence including a signal peptide (amino acid sequence of SEQ ID NO: 3), which includes a signal sequence).

The nucleic acid of the present invention can be prepared in an isolated state by using a standard genetic engineering technique, a molecular biological technique, a biochemical technique and the like with reference to sequence information disclosed in the present specification or attached sequence list.

In another embodiment of the present invention, there is provided a nucleic acid which is equivalent in function of a protein encoded thereby, but partially different in base sequence, when compared with the base sequence of the gene encoding the present enzyme (hereinafter, referred to also as "equivalent nucleic acid"; the base sequence defining the equivalent nucleic acid is referred to as "equivalent base sequence"). Examples of the equivalent nucleic acid can include a DNA composed of a base sequence containing substitution, deletion, insertion, addition, or inversion of one or more bases based on the base sequence of the nucleic acid encoding the present enzyme, and encoding a protein having the enzymatic activity characteristic of the present enzyme (i.e., random transesterification activity). Substitution or deletion of bases may occur at a plurality of sites. The term "plurality" as used herein refers to, for example, 2 to 40 bases, preferably 2 to 20 bases, more preferably 2 to 10 bases, although the number of bases varies depending on the positions and types of amino acid residues in the three-dimensional structure of the protein encoded by the nucleic acid.

The equivalent nucleic acid shows a 60% or more identity for example, preferably a 70% or more identity, more preferably a 80% or more identity, more and more preferably a 85% or more identity, much more preferably a 90% or more identity, even more preferably 95% or more identity, and most preferably a 99% or more identity with the reference base sequence (the sequence of SEQ ID NO:4 or the sequence of SEQ ID NO:5).

The equivalent nucleic acid as described above is obtained, for example, by mutation introduction through restriction enzyme treatment, treatment with an exonuclease or a DNA ligase, site-directed mutagenesis (Molecular Cloning, Third Edition, Chapter 13, Cold Spring Harbor Laboratory Press, New York), or random mutagenesis (Molecular Cloning, Third Edition, Chapter 13, Cold Spring Harbor Laboratory Press, New York). The equivalent nucleic acid can also be obtained by other methods such as UV irradiation.

Another embodiment of the present invention relates to a nucleic acid having a base sequence complementary to the base sequence of the gene encoding the present enzyme. Still another embodiment of the present invention provides a nucleic acid having a base sequence having at least about 60%, 70%, 80%, 90%, 95%, 99%, or 99.9% identity with the base sequence of the gene encoding the present enzyme of the present invention or a base sequence complementary thereto.

Yet another embodiment of the present invention relates to a nucleic acid having a base sequence that is hybridized, under stringent conditions, with a base sequence complementary to the base sequence of the gene encoding the present enzyme or an equivalent base sequence thereto. The term "stringent conditions" as used herein refers to conditions under which so-called specific hybrid is formed and non-specific hybrid is not formed. Such stringent conditions are known to those skilled in the art, and can be set, for example, with reference to Molecular Cloning (Third Edition, Cold Spring Harbor Laboratory Press, New York) and Current protocols in molecular biology (edited by Frederick M. Ausubel et al., 1987). Examples of the stringent conditions can include a condition that incubation is performed at about 42° C. to about 50° C. using a hybridization solution (50% formamide, 10×SSC (0.15 M NaCl, 15 mM sodium citrate, pH 7.0), 5×Denhardt solution, 1% SDS, 10% dextran sulfate, 10 µg/ml of denatured salmon sperm DNA, and 50 mM phosphate buffer solution (pH 7.5)), followed by washing at about 65° C. to about 70° C. using 0.1×SSC and 0.1% SDS. Examples of more preferred stringent conditions can include a condition of using, as a hybridization solution, 50% formamide, 5×SSC (0.15 M NaCl, 15 mM sodium citrate, pH7.0), 1×Denhardt solution, 1% SDS, 10% dextran sulfate, 10 µg/ml of denatured salmon sperm DNA, and 50 mM phosphate buffer solution (pH 7.5).

Still another embodiment of the present invention provides a nucleic acid (nucleic acid fragment) having a part of the base sequence of the gene encoding the present enzyme or a base sequence complementary thereto. Such a nucleic acid fragment can be used for detecting, identifying, and/or amplifying the nucleic acid having the base sequence of the gene encoding the present enzyme. The nucleic acid fragment is designed, for example, so as to include at least a portion that is hybridized with a continuous nucleotide portion in the base sequence of the gene encoding the present enzyme (for example, about 10 to about 100 bases in length, preferably about 20 to about 100 bases in length, more preferably about 30 to about 100 bases in length). When used as a probe, the nucleic acid fragment can be labeled. For labeling, for example, a fluorescent substance, an enzyme, or a radioisotope can be used.

Another aspect of the present invention relates to a recombinant DNA containing the gene of the present invention (the gene encoding the present enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8, pTrc), etc. as a vector having *Escherichia coli* as a host, pYepSec1, pMFa, pYES2, pPick3.5k and the like as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

As host cells, from the viewpoint of easy handling, microorganisms such as bacteria (e.g., *Escherichia coli*, the genus *Bacillus* (e.g., *Bacillus subtilis*)), yeast (e.g., the genus *Saccharomyces* (e.g., *Saccharomyces cerevisiae*), the genus *Pichia* (e.g., *Pichia pastoris*)), filamentous fungi (e.g., the genus *Aspergillus* (e.g., *Aspergillus oryzae*)), and actinomycetes (e.g., the genus *Streptomyces*) are preferably used, but any host cells can be used as long as they can replicate a recombinant DNA and express the gene of the present enzyme. Examples of *Escherichia coli* can include *Escherichia coli* BL21 (DE3) when the T7 promoter is used, and *Escherichia coli* JM109 and DH5a otherwise. In addition, examples of the yeast can include budding yeast SHY2, budding yeast AH22 and budding yeast INVSc1 (Invitrogen), and yeast *Pichia pastris* GS115 (Thermo Fisher Scientific K.K.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, electroporation (Potter, H. et al., Proc. Natl. Acad. Sci. U.S.A. 81, 7161-7165 (1984)), and lipofectin (Felgner, P. L. et al., Proc. Natl. Acad. Sci. U.S.A. 84, 7413-7417 (1984)). The microorganism of the present invention can be used for producing the present enzyme.

5. Method for Manufacturing the Present Enzyme

A further aspect of the present invention provides a method for manufacturing the present enzyme. A first embodiment of the manufacture method according to the present invention involves a step (step (1)) of culturing a producer microorganism for the present enzyme and a step (step (2)) of collecting a lipase from a culture solution and/or cell bodies after the culture. The producer microorganism for the present enzyme is *Candida pararugosa*, preferably a *Candida pararugosa* NBRC 0966 strain or a mutant strain thereof. The mutant strain can be obtained, for example, by irradiation with ultraviolet rays, X rays, γ rays, or the like, or treatment with nitrous acid, hydroxylamine, N-methyl-N'-nitro-N-nitrosoguanidine, or the like. The mutant strain is not limited as long as it produces the present enzyme. Examples of the mutant strain include strains with improved productivity of the present enzyme, strains with reduced productivity of contaminants, strains which are easily cultured, and strains which are easily collected from a culture solution.

Conditions and methods for culturing cells of are not particularly limited, as long as the inventive enzyme is produced. Thus, methods and culture conditions that are suitable for culturing a microorganism to be used can be set as appropriate, with the proviso that the inventive enzyme is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of microorganisms to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 20 days (preferably 3 to 10 days). An example of the culture method may include a shake culture method, and an aerobic submerged culture method by using a jar fermenter.

After culturing under the above conditions, the target protein is collected from the culture solution or the cell bodies (step (2)). When it is collected from the culture solution, the present enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the preset enzyme can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

The degree of purification of the enzyme is not particularly limited. For example, the enzyme can be purified into a state of having a specific activity of 0.5 to 20 (U/mg), preferably a specific activity of 5 to 20 (U/mg). The final form of the enzyme may be a liquid form or a solid form (including a powder form).

In another embodiment of the present invention, the present enzyme is produced by using the above-mentioned transformant. In the production method in this embodiment, the transformant is cultured under the conditions such that a protein encoded by a gene introduced therein is produced (step (i)). The culture conditions of transformant are known as to various vector-host systems, and a person skilled in the art can easily set an appropriate culture condition. Following to the culturing step, the produced protein (the present enzyme) is collected (step (ii)). Collection and following purification can be conducted in the same manner as the above embodiment.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and collection of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

6. Use of the Present Enzyme (Random Transesterification Method for Oils and Fats)

A further aspect of the present invention relates to use of the present enzyme, and provides a random transesterification method for oils and fats using the present enzyme. In the random transesterification method of the present invention, the present enzyme is used as a catalyst. In other words, in the present invention, a step of allowing the present enzyme to act on oils and fats is carried out to perform random transesterification of the oils and fats, that is, to reorganize (rearrange) constituent fatty acids of triacylglycerol (abbreviated as TG or TAG) in the oils and fats.

Examples of the oils and fats that can be treated by the random transesterification method of the present invention can include vegetable oils and fats such as soybean oil, rapeseed oil, rice oil, corn oil, sunflower oil, cottonseed oil, peanut oil, safflower oil, palm oil, palm soft oil, palm fractionated oil, palm kernel oil, coconut oil, and cacao butter, animal oils and fats such as fish oil, lard, beef tallow, and milk fat, and fractionated oils and hydrogenated oils thereof, and synthetic oils and fats such as trilaurin, triolein, and tripalmitin. The random transesterification method of the present invention can be used in transesterification between oils or fats, and also in transesterification between oils or fats and fatty acids or fatty acid esters. Examples of the fatty acids include stearic acid, palmitic acid, lauric acid, arachidic acid, behenic acid, oleic acid, and linoleic acid, and examples of the fatty acid esters include ethyl stearate, ethyl palmitate, ethyl oleate, and ethyl linoleate.

The random transesterification method of the present invention involves adding the present enzyme to oils and fats (an enzyme preparation containing the present enzyme may be added) to cause a reaction, for example, at 30 to 100° C., preferably at 35 to 80° C. for a predetermined time (for example, 5 to 48 hours). In order to accelerate the reaction, stirring may be performed during the reaction.

The immobilized present enzyme may be used as the present enzyme to be subjected to the reaction. A batch stirred tank reactor, a flow stirred tank reactor, a packed bed reactor, a fluidized bed reactor, and the like can be used for the reaction with the immobilized enzyme.

The random transesterification method of the present invention is useful for modifying and improving the physical properties of oils and fats or processed products of oils and fats (for example, shortening and margarine). For example, the random transesterification method of the present invention can be applied for improving spreadability, improving emulsion stability, optimizing a solid fat content (SFC), improving solidification, selectively concentrating specific fatty acids, producing low-trans acid oils and fats or processed products of low-trans acid oils and fats, or the like. The oils and fats or oil- and fat-processed products containing the oils and fats obtained by applying the random transesterification method of the present invention have improved physical properties as compared with those before treatment, and are of high industrial utility value.

As is clear from the above description, random transesterified oils and fats can be manufactured according to the random transesterification method of the present invention. That is, the present invention also provides a method for manufacturing a random transesterified oil or fat. Typically, the method for manufacturing a random transesterified oil or fat according to the present invention involves a step of providing an acceptor substrate (an oil or fat (triglyceride), glycerin fatty acid ester (diglyceride or monoglyceride), or glycerin) and a donor substrate (fatty acid, an ester compound (fatty acid ester or the like), or an oil or fat (which may be the same as the acceptor substrate)) and a step of allowing the enzyme of the present invention to act (that is, an enzymatic reaction in the presence of the acceptor substrate and the donor substrate). The oils and fats, fatty acids, and fatty acid esters used in the acceptor substrate and the donor substrate can be those described above. As the conditions for the enzymatic reaction, the above-mentioned conditions (for example, the reaction is caused under conditions of 30 to 100° C., preferably 35 to 80° C. for a predetermined time (for example, 5 to 48 hours)) can be adopted.

Examples

<Lipase Activity Measurement Method>

Unless otherwise specified, the lipase activity (hydrolysis activity) was measured using Lipase Kit S (manufactured by DS Pharma Co., Ltd.) according to the manual attached to the kit. However, the buffer solution used was an attached buffer solution adjusted to pH 7, and the reaction termination solution used was acetone. The lipase activity was calculated using the following calculation formula.

$$U/mL = (A412\ sample - A412\ blank) \times 1/0.05 \times n$$

(wherein A412 sample is the absorbance at 412 nm of a sample, A412 blank is the absorbance at 412 nm of a blank, 0.05 is the amount (mL) of the sample added, and n is the dilution rate.)

<Measurement of pH Stability>

The following buffer solutions were used: a 1 M glycine-hydrochloric acid buffer solution (pH 2 or 3), a 1 M citrate buffer solution (pH 3, 4, 5, or 6), a 1 M phosphate buffer solution (pH 6, 7, or 8), a 1 M Tris-hydrochloric acid buffer solution (pH 8 or 9), and a 1 M sodium carbonate buffer solution (pH 9, 10, or 11). An enzyme solution was mixed with an equal amount of each of the buffer solutions and treated at 30° C. for 1 hour. Using the treated sample, the lipase activity was measured by the following method. First, to 0.45 mL of a 0.5 M PIPES solution (pH 7), 0.05 mL of the undiluted color developing solution of Lipase Kit S and 0.05 mL of the substrate solution of Lipase Kit S were added, and the mixture was warmed at 30° C. for 5 minutes. Next, 0.025 mL of the enzyme solution was added and allowed to react for exactly 15 minutes, and then 1 mL of ethanol was added to stop the reaction. The supernatant was collected by centrifugation, and the absorbance (412 nm) was measured. The lipase activity was calculated using the above calculation formula.

<Measurement of Optimum pH>

As the buffer solution, a 20 mM Britton-Robinson's buffer solution (pH 2, 3, 4, 5, 6, 7, 8, or 9) was used. To 0.45 mL of each of the buffer solutions, 0.05 mL of the undiluted color developing solution of Lipase Kit S and 0.05 mL of the substrate solution of Lipase Kit S were added, and the mixture was warmed at 30° C. for 5 minutes. The enzyme solution (0.025 mL) was added and allowed to react for exactly 15 minutes, and then 1 mL of the reaction termination solution of Lipase Kit S was added to stop the reaction. Immediately after addition of 1 mL of 1 M Tris-HCl (pH 9), the absorbance (412 nm) was measured. The lipase activity was calculated using the above calculation formula.

<Random Transesterification Activity Measurement Method>

The enzyme solution was freeze-dried, 1 mL of cacao butter (manufactured by Daito Cacao Co., Ltd.) and 2 µL of ultrapure water were added per U of the enzyme (lipase activity), and the mixture was allowed to react at 60° C. with stirring. The reaction solution was sampled at each measurement time, and 10 µL thereof was dissolved in 1 mL of hexane to prepare a sample for gas chromatography. Gas chromatographic analysis (column: DB-1HT (J & W, 5 m×0.25 mm, and df: 0.1 µm); temperature condition: 120° C., held for 4 minutes, then raised to 150° C. at a rate of 20° C./min, further held for 3 minutes after raised to 315° C. at a rate of 30° C./min, then raised to 325° C. at a rate of 1.5° C./min, and held for 2 minutes after raised to 370° C. at a rate of 30° C./min; detector: FID; and carrier gas: helium) was performed to calculate the composition ratio of tripalmitin (C48) (PPP) in the triglyceride molecular species, and the random transesterification ability of each enzyme was evaluated using, as an index, the increase in production ratio of C48, i.e., "(composition ratio of PPP in triglyceride fraction of reacted oil or fat)−(composition ratio of PPP in triglyceride fraction of substrate oil or fat)" (ΔPPP (%)).

<Evaluation of Thermal Stability in Oil and Fat>

(1) Evaluation of Temperature Stability

Tricaprylin (manufactured by Wako Pure Chemical Industries, Ltd.) (0.5 mL) was added to freeze-dried enzyme powder corresponding to 1 U and well suspended. Heat treatment was performed at each temperature for 1 hour. After pre-incubation of each of the solutions at 60° C. for 10 minutes, 0.5 mL of methyl stearate (manufactured by Wako Pure Chemical Industries, Ltd.) preheated at 60° C. was added and well suspended, and an enzymatic reaction was performed at 60° C. for 2 hours. The solution (30 µL) after the reaction was dissolved in 1 mL of hexane to prepare a sample for gas chromatography.

Gas chromatographic analysis (column: DB-1HT (J & W, 5 m×0.25 mm, and df 0.1 µm); temperature condition: 50° C., held for 1 minute, and then raised to 370° C. at a rate of 40° C./min; detector: FID; and carrier gas: helium) was performed to determine an area value of the amount of methyl caprylate produced as a result of the enzymatic reaction (transesterification), and comparison was made in terms of the residual activity of the sample to an untreated sample.

(2) Evaluation of Reactivity in Oil and Fat

Enzyme powder (freeze-dried product) corresponding to 5 U was suspended in cacao butter, and 2 μL of purified water was added per mL of cacao butter to start the reaction. The amounts of tripalmitin produced 8 hours after the start of the reaction, at the respective reaction temperatures, were compared with each other.

1. Screening

Approximately 1500 strains including bacteria, yeast, filamentous fungi, and actinomycetes were subjected to screening in order to find strains showing random transesterification activity. In primary screening, each strain was grown on each plate containing 0.5% soybean oil to form a halo, and then further incubated at 55° C., and strains with an expanded halo were selected as heat-resistant lipase-producer strain.

In secondary screening, culture solutions obtained by liquid-culturing the strains selected in the primary screening were pulverized by vacuum drying at 60° C., 1 mL of cacao butter and 2 μl of water were added, and the mixtures were allowed to react for 8 days. The strains (Table 1) in which the production of tripalmitin as an index for random transesterification could be confirmed by gas chromatography (GC) were subjected to next screening.

TABLE 1

| NO. | Strains | ΔPPP(%) |
|---|---|---|
| 1 | Candida nitrativorans | 0.73 |
| 2 | Candida sp | 0.03 |
| 3 | Pichia cf silvicola | 0.09 |
| 4 | Penicillium resticulosum | 0.09 |
| 5 | Rhizopus cf. oryzae | 0.09 |
| 6 | Thermomyces cf. lanuginosus | 0.41 |
| 7 | Pichia xylosa | 0.08 |
| 8 | Pichia anomala | 0.04 |
| 9 | Candida pararugosa | 0.35 |
| 10 | Rhodotorula glutinis | 0.05 |
| 11 | Geobacillus sp. | 0.07 |
| 12 | Rhizopus oryzae | 1.41 |
| 13 | Rhizomucor miehei | 0.21 |

In tertiary screening, evaluation was made based on the amount of tripalmitin produced similarly as in the secondary screening (reaction for 12 days) under the condition that the enzyme activity was constant (6 U). As a result, the *Candida pararugosa* NBRC 0966 strain was found as a strain having high random transesterification activity.

2. Acquisition of Crude Enzyme

In a 500-mL Sakaguchi flask, 100 mL of the preculture medium was placed. After steam sterilization, 1 platinum loop of the *Candida pararugosa* NBRC 0966 strain was inoculated and cultured at 27° C. for 4 days to obtain a preculture solution.

<Preculture Medium>

Yeast extract (manufactured by Becton Dickinson Co., Ltd.): 0.3%

Malto extract (manufactured by Becton Dickinson Co., Ltd.): 0.3%

Bacto Peptone (manufactured by Becton Dickinson Co., Ltd.): 0.5%

Hydrous crystalline glucose: 1.0%

Soybean salad oil: 0.5% pH 6.2

A main culture medium was placed in a jar fermenter with a volume of 30 L, and, after steam sterilization, the preculture solution was added. The strain was cultured at 27° C., a stirring rate of 250 rpm, and an aeration rate of 0.5 vvm for 4 days to obtain a culture solution.

<Main Culture Medium>

Yeast extract (manufactured by Becton Dickinson Co., Ltd.): 0.9%

Malto extract (manufactured by Becton Dickinson Co., Ltd.): 0.9%

Peptone (manufactured by Becton Dickinson Co., Ltd.): 1.5%

Hydrous crystalline glucose (manufactured by San-ei Sucrochemical Co., Ltd.): 3.0%

Soybean salad oil (manufactured by The Nisshin Oillio Group, Ltd.): 1.5% pH 6.2

The obtained culture solution was centrifuged to collect a culture supernatant. The culture supernatant was subjected to diatomaceous earth filtration to obtain a clear solution. The clear solution was concentrated and desalted by ultrafiltration, and the resulting desalted solution (crude enzyme solution) was freeze-dried to obtain a crude enzyme powder. A part of the crude enzyme solution was used for enzyme purification.

3. Evaluation of Enzymological Properties (1) pH Stability and Optimum pH

Figure 2:
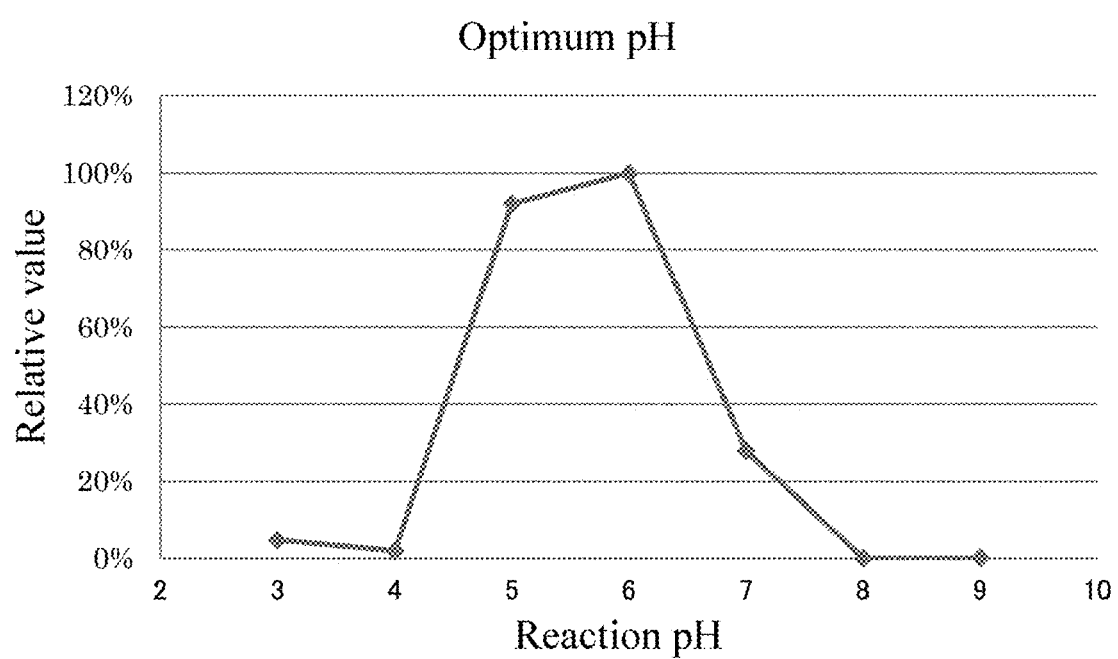
FIG. 2 Optimum pH of the novel lipase derived from the *Candida pararugosa* NBRC 0966 strain.

The crude enzyme powder was dissolved in water to yield an enzyme solution. Using the enzyme solution, the pH stability and optimum pH were measured by the above-mentioned measurement methods. The measurement results are shown in FIG. 1 (pH stability) and FIG. 2 (optimum pH). High activity was maintained at a pH of 3 to 7 (80% or more remained after treatment at 30° C. for 1 hour), and the optimum pH was 6.

(2) Temperature Stability and Reactivity in Oil and Fat

Figure 3:
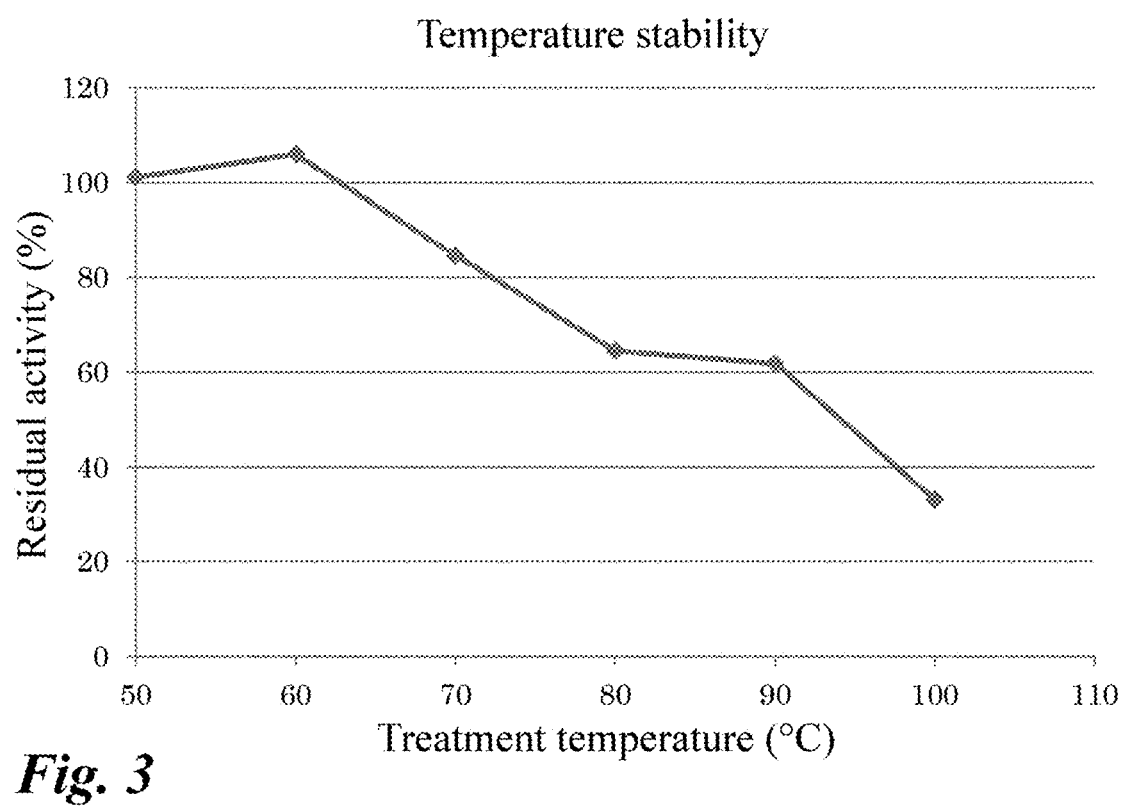
FIG. 3 Temperature stability of the novel lipase derived from the *Candida pararugosa* NBRC 0966 strain. Comparison was made in terms of the temperature stability, based on the amount of methyl caprylate produced by a reaction using tricaprylin and methyl stearate as substrates after treatment in tricaprylin at each temperature for 1 hour.
Figure 4:
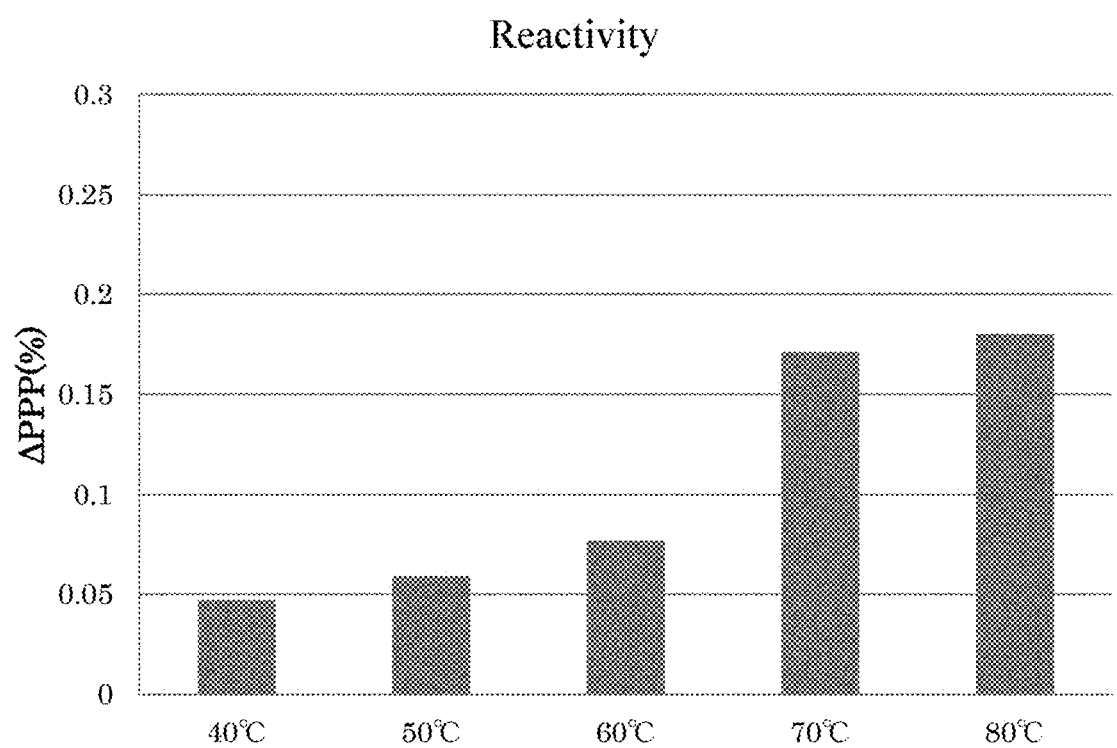
FIG. 4 Reactivity of the novel lipase derived from the *Candida pararugosa* NBRC 0966 strain. Comparison was made in terms of the reactivity, based on the amount of tripalmitin (PPP) produced after a reaction for 8 hours at each reaction temperature.

The crude enzyme powder was used to evaluate the temperature stability and reactivity in oils and fats by the above-mentioned evaluation methods. The results are shown in FIG. 3 (temperature stability) and FIG. 4 (reactivity). The enzyme was stable up to 60° C. (in the case of treatment in tricaprylin for 1 hour, 90% or higher activity was maintained at 60° C. or lower), the temperature stability of which was excellent. In the oils and fats, the highest reactivity was exhibited at 80° C. in the range of 40 to 80° C.

4. Purification of Enzyme and Measurement of Molecular Weight

Figure 5:
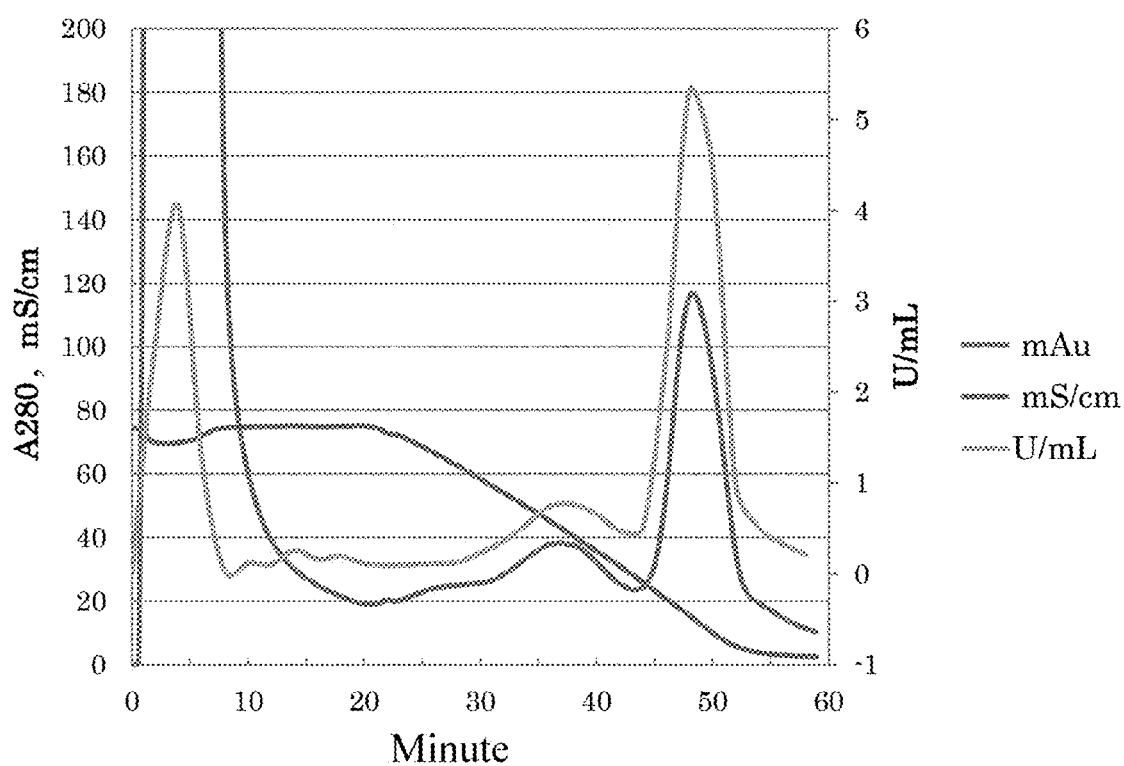
FIG. 5 A hydrophobic chromatography purification chart.

The crude enzyme solution was subjected to hydrophobic chromatography (Butyl-HP (manufactured by GE Healthcare Ltd.)). The column was equilibrated with a 20 mM phosphate buffer solution (pH 7.0) and elution was performed with a linear gradient (30 CV) of ammonium sulfate (0.5 to 0 M). Fractionation was performed using the lipase activity (hydrolysis activity) as an index. The purification chart is shown in FIG. 5. Since a plurality of fractions having the lipase activity could be confirmed, these fractions were subjected to SDS-PAGE. On the other hand, a fraction with peak activity (active main peak fraction) was treated with Endo-Hf (manufactured by New England Biolabs) (removal of N-glycans), and the molecular weights before and after treatment were compared by SDS-PAGE.

Figure 6:
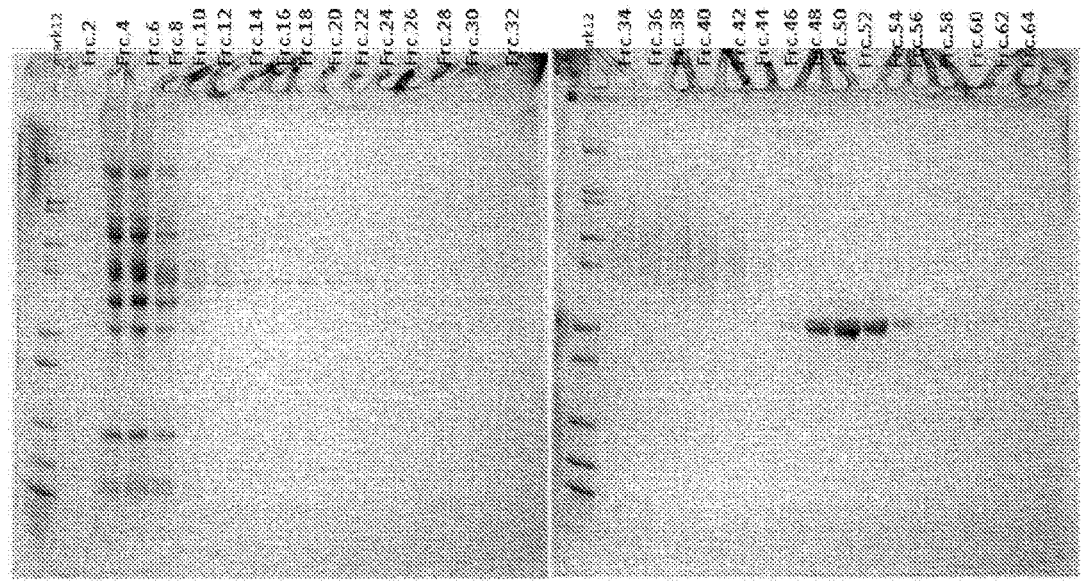
FIG. 6A Results of SDS-PAGE of hydrophobic chromatography purified fractions.
FIG. 6B: Results of End-Hf treatment of an active main peak fraction. Lane M: Molecular weight marker (manufactured by GE Healthcare Ltd.). Lane 1: Endo-Hf; Lane 2: Endo-Hf-treated active main peak fraction; and Lane 3: Endo-Hf-untreated active main peak fraction.
Figure 6:
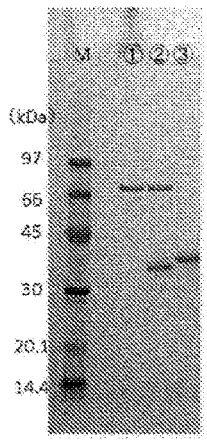

The results of SDS-PAGE of the purified fractions are shown in FIG. 6A. The results of the Endo-Hf treatment of the active main peak fractions are shown in FIG. 6B. The molecular weight of the enzyme of interest (lipase) after the Endo-Hf treatment (after the removal of N-glycans) was about 36 kDa. As a result of the analysis of the amino acid sequence of a purified enzyme, the N-terminal amino acid sequence was VTDEPLENVPGILSHPTI (SEQ ID NO: 1).

Database search was performed based on this N-terminal sequence, but no homologous protein could be found.

5. Confirmation of Random Transesterification Activity of Purified Enzyme

Figure 7:
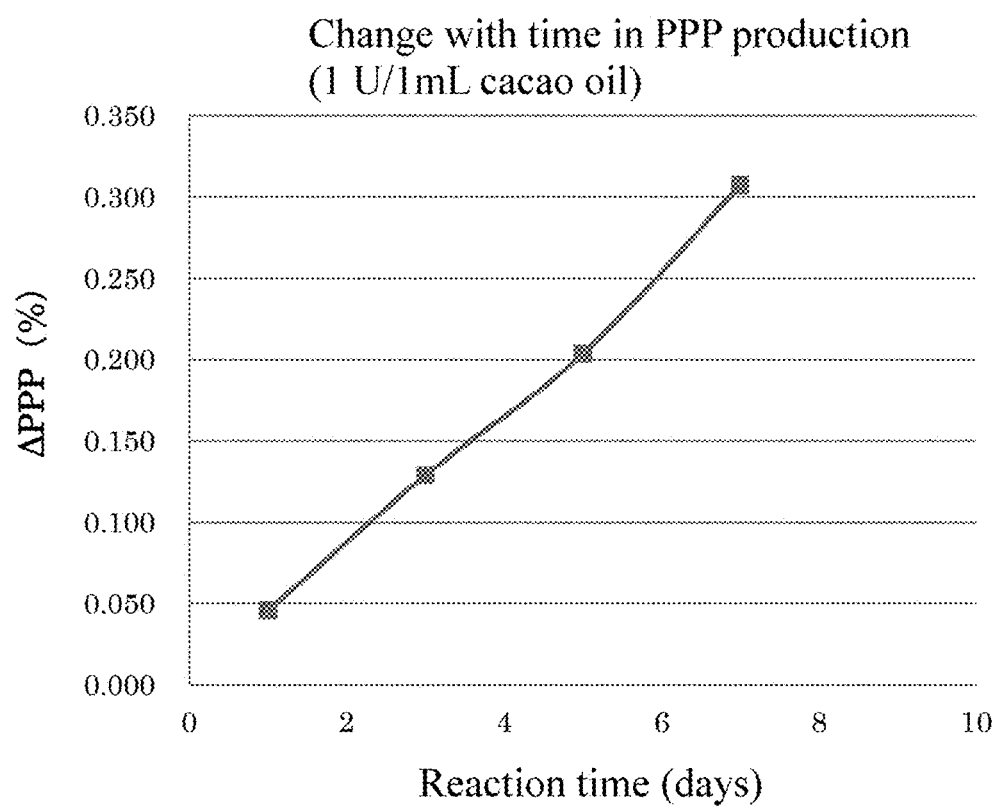
FIG. 7 Change with time in amount of tripalmitin produced by a purified enzyme.

The random transesterification activity was measured using purified fractions (obtained by collecting, and then concentrating and desalting fractions 48 to 52). As a result, production of tripalmitin (PPP) was confirmed also in the purified fractions (FIG. 7), indicating that the enzyme of interest was successfully purified.

6. Gene Cloning

The *C. pararugosa* NBRC 0966 strain was cultured in a YM medium having 0.5% soybean salad oil added (Yeast extract (Bacto): 0.9%, Malto extract (Bacto): 0.9%, Peptone (Bacto): 1.5%, hydrous crystalline glucose: 3.0%, and soybean salad oil: 1.5%) (pH 6.2) for 1 day, and cell bodies were collected by centrifugation. The collected cell bodies were thoroughly washed with a TE buffer solution (pH 8.0). The obtained cell bodies were ground under liquid nitrogen using a mortar and pestle. RNAiso Plus (manufactured by Takara Bio Inc.) was used to extract total RNA from the ground cell bodies according to the attached protocol. Then, Oligotex™-dT30<Super> mRNA Purification Kit (manufactured by Takara Bio Inc.) was used to prepare an mRNA from the extracted RNA according to the attached protocol.

SuperScript™ III First-Strand Synthesis System (manufactured by Thermo Fisher Scientific K.K.) was used to synthesize a cDNA according to the attached protocol. Using the obtained cDNA as a template, PCR was performed using a primer having homology with the upstream of the structural gene (RELFUP: 5'-CACATCTCAATAGCATCA-3': SEQ ID NO: 6) and a primer having homology with the downstream of the structural gene (RELEDOWN: 5'-AGCTGGGTATGTTCAGAAGTTAA-3': SEQ ID NO: 7) and also using PrimeSTAR (registered trademark) Max DNA Polymerase (manufactured by Takara Bio Inc.) according to the attached protocol. The amplification product of about 1000 bp in which amplification was confirmed was cloned using Mighty TA-cloning Kit (Takara Bio Inc.), and the sequence (SEQ ID NO: 5) was confirmed.

7. Recombinant Expression

Using the *Pichia* expression system, it was confirmed that the obtained cDNA was the gene of the enzyme of interest. The cDNA sequence (SEQ ID NO: 5), from the start codon to the stop codon, was amplified by PCR, and the amplification product was cloned into the snaBI site of pPick3.5k (manufactured by Thermo Fisher Scientific K.K.) according to a conventional method to produce an expression vector pPick3.5k-REL. pPick3.5k-REL was digested with restriction enzyme SalI, and a linear DNA was collected by ethanol precipitation. Using the collected DNA, *Pichia pastris* GS115 (manufactured by Thermo Fisher Scientific K.K.) was transformed by electroporation according to a standard method to obtain a transformant. The transformant was cultured in a BMGY medium (2% bactopeptone, 1% yeast extract, 1% glycerin, 0.67% yeast nitrogen base (YNB (containing ammonium sulfate and containing no amino acid)), 100 mM potassium phosphate buffer solution (pH 6.0), and 0.00004% D-biotin) at 30° C. for 2 days. The obtained cell bodies were suspended in a BMMY medium (2% bactopeptone, 1% yeast extract, 0.5% methanol, 0.67% yeast nitrogen base (YNB (containing ammonium sulfate and containing no amino acid)), 100 mM potassium phosphate buffer solution (pH 6.0), and 0.00004% D-biotin), and cultured at 30° C. for 3 days while appropriately adding methanol. The supernatant was collected by centrifugation to obtain a crude enzyme solution. The lipase activity of the obtained crude enzyme solution was confirmed according to the above method.

8. Confirmation of Random Transesterification Activity

Figure 8:
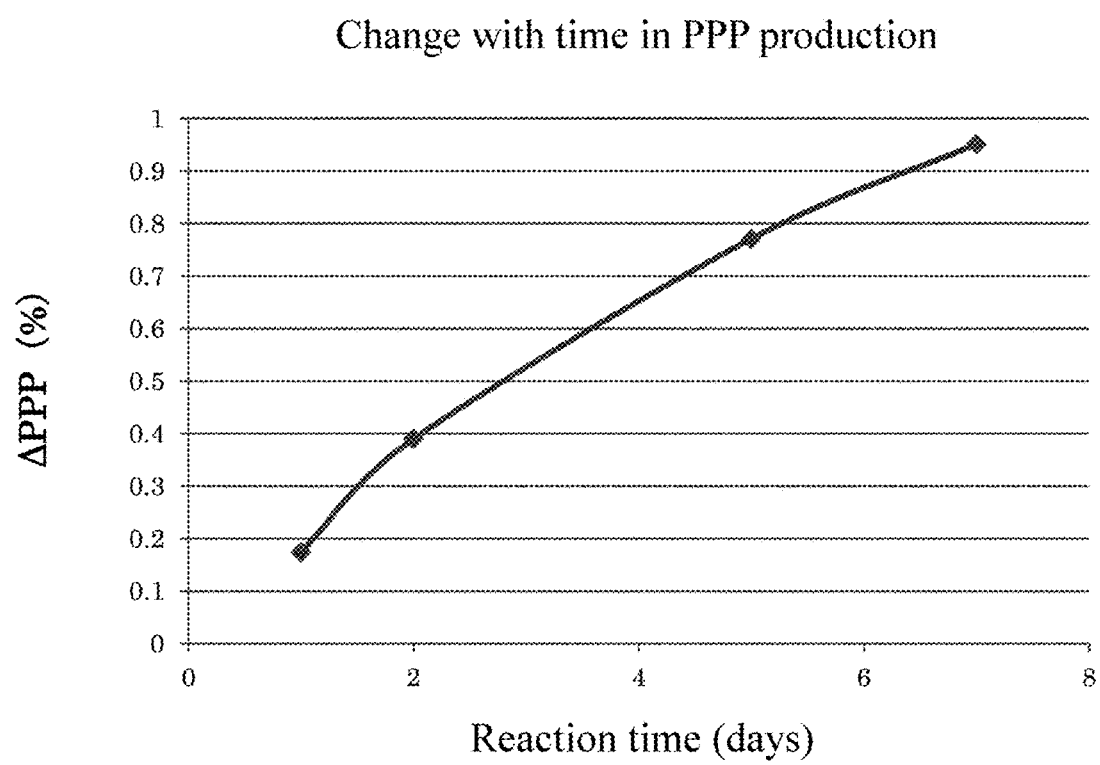
FIG. 8 Change with time in amount of tripalmitin produced by a recombinant enzyme.

The obtained crude enzyme solution was used to confirm the random transesterification activity according to the above method. The results are shown in FIG. 8. Production of tripalmitin (PPP) was observed (FIG. 8), and it was confirmed that the sequence of SEQ ID NO: 5 was of the gene (cDNA) of the enzyme of interest (lipase showing the random transesterification activity). The amino acid sequence of the enzyme of interest encoded by the sequence of SEQ ID NO: 5 is shown in SEQ ID NO: 3. Sixty three (63) bases on the 5'-terminal side of the sequence of SEQ ID NO: 5 constitute a signal sequence, and the sequence (SEQ ID NO: 4) except the signal sequence encodes the amino acid sequence (SEQ ID NO: 2) of the mature enzyme (not including the signal peptide).

INDUSTRIAL APPLICABILITY

The random transesterification lipase of the present invention has high heat resistance and is suitable for use in food applications. The random transesterification lipase of the present invention is used, for example, in modifying edible oils and fats such as margarine and shortening.

The present invention is not limited to the above description of the embodiments and examples of the present invention at all. Various modifications that can be easily achieved by those skilled in the art without departing from the claims also fall within the scope of the present invention. The contents of the articles, patent laid-open publications, patent publications, and the like specified herein shall be incorporated by reference in their entity.

The invention claimed is:

1. A random transesterification method for oils and fats, comprising a step of contacting a purified enzyme composition with oils and fats;
   wherein the purified enzyme composition comprises a lipase that catalyzes a random transesterification reaction; and
   wherein the lipase has the amino acid sequence of SEQ ID NO: 2 or an amino acid sequence having at least 90% sequence identity to the amino acid sequence of SEQ ID NO: 2.

2. The method of claim 1, wherein the lipase has the following enzymological properties:
   (1) action: catalyzing a random transesterification reaction;
   (2) molecular weight: having a molecular weight without N-glycan of about 36 kDa, wherein the molecular weight is determined by SDS-PAGE;
   (3) temperature stability in oils and fats: being stable at 60° C. or lower, wherein the temperature stability is determined using tricaprylin and methyl stearate as substrates and production of methyl caprylate as an index; and
   (4) reactivity in oils and fats: showing the highest reactivity at 80° C. when allowed to react at 40 to 80° C., wherein the reactivity in oils and fats is determined using cacao butter as a substrate and production of tripalmitin as an index.

3. The method of claim 2, wherein the lipase further has the following enzymological properties:
   (5) pH stability: being stable in a pH range of 3 to 7, wherein the pH stability is determined at 30° C. and 1 hour; and
   (6) optimum pH: 6.

4. The method of claim 1, wherein the N-terminal amino acid sequence of the lipase is VTDEPLENVPGILSHPTI (SEQ ID NO: 1).

5. The method of claim 1, wherein the lipase is derived from *Candida pararugosa*.

6. The method of claim 5, wherein the *Candida pararugosa* is *Candida pararugosa* NBRC 0966.

7. The method of claim 1, wherein the lipase has the amino acid sequence of SEQ ID NO: 2.

* * * * *

SEQUENCE LISTING

```
<160> NUMBER OF SEQ ID NOS: 7

<210> SEQ ID NO 1
<211> LENGTH: 18
<212> TYPE: PRT
<213> ORGANISM: Candida pararugosa

<400> SEQUENCE: 1

Val Thr Asp Glu Pro Leu Glu Asn Val Pro Gly Ile Leu Ser His Pro
1               5                   10                  15

Thr Ile
```

<210> SEQ ID NO 2
<211> LENGTH: 324
<212> TYPE: PRT
<213> ORGANISM: Candida pararugosa

<400> SEQUENCE: 2

```
Val Thr Asp Glu Pro Leu Glu Asn Val Pro Gly Ile Leu Ser His Pro
1               5                   10                  15

Thr Ile His Gly Phe Pro Ser Gly Gly Tyr Gly Pro Ser Gln Asp Thr
            20                  25                  30

Phe Ile Ala Ala Ser Leu Tyr Ala Lys Gly His Ile Gly Tyr Ala Pro
        35                  40                  45

Pro Gly Ser Gly Asn Ala Ser Cys Val Val Gly Glu Gly Gln Tyr Pro
    50                  55                  60

Val Val Leu Val Pro Gly Thr Val Glu Asp Ala Tyr Ser Asn Trp Ala
65                  70                  75                  80

Tyr Tyr Ser Gln Lys Leu Thr Asp Gln Gly Leu Cys Val Tyr Thr Phe
                85                  90                  95

Asn His Asn Pro Met Ser Phe Phe Gly Gln Ser Glu Val Leu Gly Ile
            100                 105                 110

Ser Leu Glu Ala Trp Pro Phe Ala Gly Asp Ile Lys Asp Ser Ala Ala
        115                 120                 125

Ala Leu Ser Gln Val Val Asp Tyr Val Leu Gln Ile Thr Gly Ala Ser
    130                 135                 140

Lys Val Asp Leu Val Gly His Ser Gln Gly Gly Gly Ala Leu Pro Ser
145                 150                 155                 160

Trp Tyr Ile Lys Lys Leu Gly Gly Ala Pro Lys Val Asn Lys Met Val
                165                 170                 175

Ala Leu Ala Gly Asp Tyr Lys Gly Thr Asn Pro Val Gly Leu Gly Ala
            180                 185                 190

Leu Leu Thr Glu Val Gly Leu Gly Thr Val Ala Asp Thr Ile Leu Asn
        195                 200                 205

Glu Ser Ile Asn Ala Glu Gly Leu Thr Gln Gln Leu Thr Gly Ser Asp
    210                 215                 220

Phe Met Lys Glu Leu Asn Asp Gly Asp Gly Pro Gly Val Ala Gly Val
225                 230                 235                 240

Arg Tyr Thr Asn Ile Ala Thr Met Tyr Asp Glu Ile Leu Ile Pro Phe
                245                 250                 255

Thr Asn Thr Trp Phe Thr Gln Asp Gly Val Asp Val Asn Asn Ile Lys
            260                 265                 270

Ile Gln Asp Tyr Cys Ala Leu Asp Phe Thr Asp His Ile Gly Phe Ala
        275                 280                 285

Tyr Asp Pro Val Ala Tyr Gln Ile Val Glu Asn Val Leu Leu Asp Lys
    290                 295                 300

Asn Asp Lys Ile Lys Cys Thr Tyr Val Pro Pro Val Phe Gln Lys Arg
305                 310                 315                 320

Glu Phe Glu Ala
```

<210> SEQ ID NO 3
<211> LENGTH: 345
<212> TYPE: PRT
<213> ORGANISM: Candida pararugosa

<400> SEQUENCE: 3

```
Met Ile Ser Ser Val Phe Leu Ser Ala Leu Ser Leu Ala Ala Ser Phe
1               5                   10                  15
```

Pro Leu Asn Lys Arg Val Thr Asp Glu Pro Leu Glu Asn Val Pro Gly
            20                  25                  30

Ile Leu Ser His Pro Thr Ile His Gly Phe Pro Ser Gly Gly Tyr Gly
        35                  40                  45

Pro Ser Gln Asp Thr Phe Ile Ala Ala Ser Leu Tyr Ala Lys Gly His
    50                  55                  60

Ile Gly Tyr Ala Pro Pro Gly Ser Gly Asn Ala Ser Cys Val Val Gly
65                  70                  75                  80

Glu Gly Gln Tyr Pro Val Val Leu Val Pro Gly Thr Val Glu Asp Ala
                85                  90                  95

Tyr Ser Asn Trp Ala Tyr Tyr Ser Gln Lys Leu Thr Asp Gln Gly Leu
            100                 105                 110

Cys Val Tyr Thr Phe Asn His Asn Pro Met Ser Phe Phe Gly Gln Ser
        115                 120                 125

Glu Val Leu Gly Ile Ser Leu Glu Ala Trp Pro Phe Ala Gly Asp Ile
    130                 135                 140

Lys Asp Ser Ala Ala Ala Leu Ser Gln Val Val Asp Tyr Val Leu Gln
145                 150                 155                 160

Ile Thr Gly Ala Ser Lys Val Asp Leu Val Gly His Ser Gln Gly Gly
                165                 170                 175

Gly Ala Leu Pro Ser Trp Tyr Ile Lys Lys Leu Gly Gly Ala Pro Lys
            180                 185                 190

Val Asn Lys Met Val Ala Leu Ala Gly Asp Tyr Lys Gly Thr Asn Pro
        195                 200                 205

Val Gly Leu Gly Ala Leu Leu Thr Glu Val Gly Leu Gly Thr Val Ala
    210                 215                 220

Asp Thr Ile Leu Asn Glu Ser Ile Asn Ala Glu Gly Leu Thr Gln Gln
225                 230                 235                 240

Leu Thr Gly Ser Asp Phe Met Lys Glu Leu Asn Asp Gly Asp Gly Pro
                245                 250                 255

Gly Val Ala Gly Val Arg Tyr Thr Asn Ile Ala Thr Met Tyr Asp Glu
            260                 265                 270

Ile Leu Ile Pro Phe Thr Asn Thr Trp Phe Thr Gln Asp Gly Val Asp
        275                 280                 285

Val Asn Asn Ile Lys Ile Gln Asp Tyr Cys Ala Leu Asp Phe Thr Asp
    290                 295                 300

His Ile Gly Phe Ala Tyr Asp Pro Val Ala Tyr Gln Ile Val Glu Asn
305                 310                 315                 320

Val Leu Leu Asp Lys Asn Asp Lys Ile Lys Cys Thr Tyr Val Pro Pro
                325                 330                 335

Val Phe Gln Lys Arg Glu Phe Glu Ala
            340                 345

<210> SEQ ID NO 4
<211> LENGTH: 975
<212> TYPE: DNA
<213> ORGANISM: Candida pararugosa

<400> SEQUENCE: 4
gttacggacg aacccttgga aaatgtccct ggaatactgt ctcaccccac tatccatggc      60
ttccctagtg gaggctatgg tccctctcaa gatactttca tagctgcttc gttgtatgcc     120
aagggccata ttggatatgc tcctcctggc tctggtaacg cttcctgcgt tgttggggag     180
gggcagtatc ctgtcgttct cgtacctggt actgtggagg acgcctactc aaactgggcg     240

```
tactactccc agaaattaac tgaccagggt ctctgtgttt acactttcaa ccacaaccca    300
atgagtttct ttgggcagag cgaggttctc ggtatctctt tggaggcatg gccatttgct    360
ggagatatta agatagtgc agctgctctt tctcaagtag tggactatgt tttgcagatt     420
accggtgcga gcaaggttga tctcgttgga cactctcagg gtggtggagc attgccaagt    480
tggtacatca agaaacttgg aggcgcccct aaggttaaca agatggttgc tcttgctggt    540
gactacaagg gcaccaaccc ggttggtctt ggggctctct tgaccgaggt aggacttggt    600
acggtggcag acacaatttt gaatgagtct attaatgctg agggtttgac ccaacaactc    660
actgggtcag acttcatgaa ggaactcaat gacggtgacg gacctggagt tgcagggggtt   720 cgctacacta acatcgctac aatgtatgat gagattctca tcccgtttac aaatacttgg    780
ttcactcaag atggagtgga tgtcaacaac atcaaaatcc aggattactg tgcactcgat    840
tttactgatc acatcggctt tgcctatgat cccgttgcat atcagatcgt tgagaacgtt    900
ttgctggaca agaacgataa gatcaagtgc acttatgtac ctcctgtgtt ccagaagcgc    960
gaatttgaag cctaa                                                    975

<210> SEQ ID NO 5
<211> LENGTH: 1038
<212> TYPE: DNA
<213> ORGANISM: Candida pararugosa

<400> SEQUENCE: 5
atgatctcga gcgtcttcct ctctgcactc tctcttgctg cctccttctcc gctgaacaag    60 cgtgttacgg acgaaccctt ggaaaatgtc cctggaatac tgtctcaccc cactatccat   120
ggcttcccta gtggaggcta tggtccctct caagatactt tcatagctgc ttcgttgtat   180
gccaagggcc atattggata tgctcctcct ggctctggta acgcttcctg cgttgttggg   240
gaggggcagt atcctgtcgt ctcgtacct ggtactgtgg aggacgccta ctcaaactgg    300
gcgtactact cccagaaatt aactgaccag ggtctctgtg tttacacttt caaccacaac    360
ccaatgagtt tctttgggca gagcgaggtt ctcggtatct cttttggaggc atggccattt   420 gctggagata ttaaagatag tgcagctgct cttttctcaag tagtggacta tgttttgcag   480
attaccggtg cgagcaaggt tgatctcgtt ggacactctc agggtggtgg agcattgcca   540
agttggtaca tcaagaaact tggaggcgcc cctaaggtta acaagatggt tgctcttgct   600
ggtgactaca agggcaccaa cccggttggt cttgggctc tcttgaccga ggtaggactt    660
ggtacggtgg cagacacaat tttgaatgag tctattaatg ctgagggttt gacccaacaa    720
ctcactgggt cagacttcat gaaggaactc aatgacggtg acggacctgg agttgcaggg    780
gttcgctaca ctaacatcgc tacaatgtat gatgagattc tcatcccgtt tacaaatact    840
tggttcactc aagatggagt ggatgtcaac aacatcaaaa tccaggatta ctgtgcactc    900
gattttactg atcacatcgg ctttgcctat gatcccgttg catatcagat cgttgagaac    960
gttttgctgg acaagaacga taagatcaag tgcacttatg tacctcctgt gttccagaag   1020
cgcgaatttg aagcctaa                                                1038

<210> SEQ ID NO 6
<211> LENGTH: 18
<212> TYPE: DNA
<213> ORGANISM: Artificial Sequence
<220> FEATURE:
<223> OTHER INFORMATION: forward primer
```

```
<400> SEQUENCE: 6
cacatctcaa tagcatca                                          18

<210> SEQ ID NO 7
<211> LENGTH: 23
<212> TYPE: DNA
<213> ORGANISM: Artificial Sequence
<220> FEATURE:
<223> OTHER INFORMATION: reverse primer

<400> SEQUENCE: 7
agctgggtat gttcagaagt taa                                    23
```